United States Patent
Palkowitz

[19]
[11] Patent Number: 5,977,098
[45] Date of Patent: *Nov. 2, 1999

[54] BENZO[B]THIOPHENE COMPOUNDS, INTERMEDIATES, PROCESSES, COMPOSITIONS, AND METHODS

[75] Inventor: Alan David Palkowitz, Carmel, Ind.

[73] Assignee: Eli Lilly and Company, Indianapolis, Ind.

[*] Notice: This patent is subject to a terminal disclaimer.

[21] Appl. No.: 09/107,344

[22] Filed: Jun. 30, 1998

Related U.S. Application Data

[62] Division of application No. 08/924,772, Aug. 27, 1997, Pat. No. 5,843,965
[60] Provisional application No. 60/025,124, Aug. 29, 1996.

[51] Int. Cl.⁶ .................. A61K 31/445; A61K 31/38; C07D 333/64; C07D 409/12
[52] U.S. Cl. .................. 514/212; 549/52; 549/54; 549/56; 548/525; 546/202; 544/145; 540/596; 514/324; 514/233.5; 514/422; 514/443
[58] Field of Search .................. 549/52, 54, 56; 514/443, 422, 324, 233.5, 212; 540/596; 544/145; 546/202; 548/525

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,798 | 1/1996 | Bryant et al. | 514/324 |
| 5,488,058 | 1/1996 | Palkowitz | 514/324 |
| 5,492,922 | 2/1996 | Palkowitz | 514/324 |
| 5,510,357 | 4/1996 | Palkowitz | 514/324 |
| 5,510,358 | 4/1996 | Palkowitz | 514/324 |
| 5,510,498 | 4/1996 | Palkowitz | 549/52 |
| 5,843,965 | 12/1998 | Palkowitz | 514/234 |

FOREIGN PATENT DOCUMENTS

| | | |
|---|---|---|
| 0584 952 | 3/1961 | European Pat. Off. . |
| 062 503 | 10/1982 | European Pat. Off. . |
| 0605 193 | 7/1994 | European Pat. Off. . |
| 0617 030 | 9/1994 | European Pat. Off. . |
| 0652 005 | 5/1995 | European Pat. Off. . |
| 0729 956 | 4/1996 | European Pat. Off. . |
| 0731 100 | 9/1996 | European Pat. Off. . |
| WO 89/0289 | 4/1989 | WIPO . |
| WO 95/10513 | 4/1995 | WIPO . |

OTHER PUBLICATIONS

Crenshaw, R.R., et al, *J. Med. Chem.* 14(12):1185–1190 (1971).
Jones, C.D., et al, *J. Med. Chem.* 27: 1057–1066) 1984.
Jones, C.D., et al, *J. Med. Chem.* 35: 931–938 1992.

*Primary Examiner*—Mukund J. Shah
*Assistant Examiner*—Ann M. Kessinger
*Attorney, Agent, or Firm*—Gilbert T. Voy

[57] ABSTRACT

The invention provides a compound of formula I:

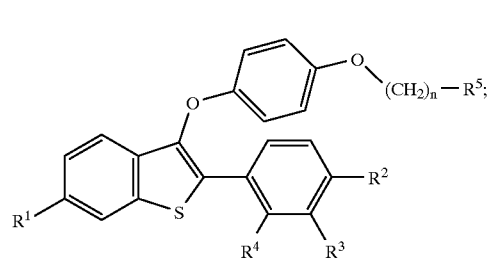

or a pharmaceutically acceptable salt or solvate thereof; pharmaceutical formulations containing a compound of formula I, and methods of using a compound of formula I for the inhibition of bone loss or bone resorption and for treatment of cardiovascular-related pathological conditions.

10 Claims, No Drawings

BENZO[B]THIOPHENE COMPOUNDS, INTERMEDIATES, PROCESSES, COMPOSITIONS, AND METHODS

This application is a divisional of application Ser. No. 08/924,772, filed Aug. 27, 1997 now U.S. Pat. No. 5,843,965, which claims the benefit of U.S. Provisional Application No. 60/025,124, filed Aug. 29, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

In response to the clear need for new pharmaceutical agents which are capable of alleviating the symptoms of, inter alia, postmenopausal syndrome, the present invention provides benzo[b]thiophene compounds, pharmaceutical formulations thereof, and methods of using such compounds for the treatment of postmenopausal syndrome and other estrogen-related pathological conditions such as those mentioned below.

Thus, it would be a significant contribution to the art to provide novel benzo[b]thiophene compounds useful, for example, in the inhibition, treatment, or prevention of the disease states as indicated herein.

SUMMARY OF THE INVENTION

The present invention relates to compounds of formula I

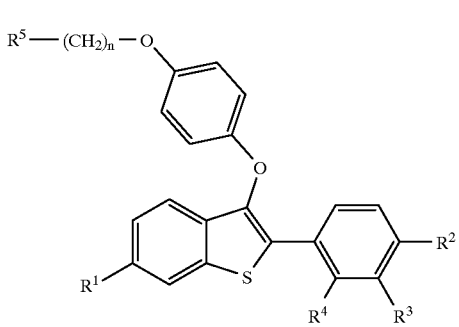

wherein:
$R^1$ is —H, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^2$ is —H, —F, —Cl, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^3$ and $R^4$ are, independently, —H, —F, —Cl, —CH$_3$, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl), with the proviso that $R^3$ and $R^4$ are not both hydrogen;

n is 2 or 3; and $R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino;

or a pharmaceutically acceptable salt or solvate thereof.

Also provided by the present invention are methods of using compounds of formula I, formulations containing formula I and intermediates useful in the preparation of compounds of formula I.

DETAILED DESCRIPTION OF THE INVENTION

The instant invention also provides intermediate compounds of formula II which are useful for preparing the pharmaceutically active compounds of the present invention

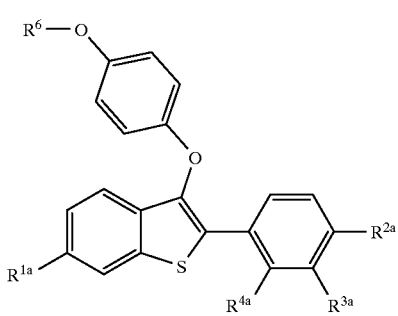

II wherein:

$R^{1a}$ is —H or —OR$^7$;

$R^{2a}$, $R^{3a}$, and $R^{4a}$ are, independently, —H, —F, —Cl, or —OR$^7$, with the proviso that $R^{3a}$ and $R^{4a}$ are not both hydrogen;

$R^6$ is —H or —R$^8$; and $R^7$ and $R^8$ are hydroxy-protecting groups which can be selectively removed in the presence of each other.

The present invention also provides intermediate compounds of formula III which are useful in the preparation of the pharmaceutically active compounds of the present invention

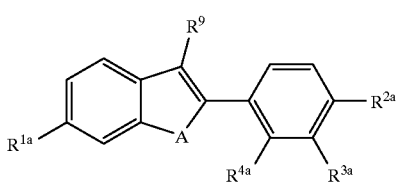

III wherein:

$R^{1a}$, $R^{2a}$, $R^{3a}$, and $R^{4a}$ have their previous meanings, with the proviso that $R^{3a}$ and $R^{4a}$ are not both hydrogen;

A is sulfur or sulfoxide; and $R^9$ is a halogen.

The present invention also provides intermediate compounds of formula IV useful in the synthesis of pharmaceutically active compounds of formula I

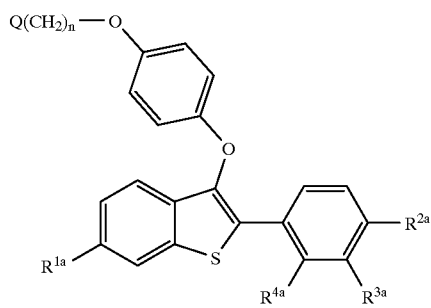

IV wherein:

$R^{1a}$, $R^{2a}$, $R^{3a}$, $R^{4a}$, and n have their previous meanings, with the proviso that $R^{3a}$ and $R^{4a}$ are not both hydrogen; and Q is a leaving group.

The present invention further provides pharmaceutical formulations containing compounds of formula I, optionally containing an effective amount of an additional therapeutic agent selected from the group consisting of estrogen, progestin, bisphosphonate, PTH, and subcombinations thereof, and the use of said compounds and/or subcombinations at least for the inhibition of bone loss or bone resorption, particularly osteoporosis and cardiovascular-related pathological conditions including hyperlipidemia and related cardiovascular pathologies.

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—O($C_1$–$C_4$ alkyl)" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is preferred.

The term "substituted phenyl" refers to a phenyl group having one or more substituents selected from the group consisting of $C_1$–$C_4$ alkyl, $C_1$–$C_3$ alkoxy, hydroxy, nitro, chloro, fluoro, tri(chloro or fluoro)methyl, and the like. "$C_1$–$C_4$ alkoxy" refers to a $C_1$–$C_4$ alkyl group attached through an oxygen bridge, such as methoxy, ethoxy, n-propoxy, and isopropoxy, butoxy, and the like. Of these $C_1$–$C_4$ alkoxy groups, methoxy is highly preferred.

The term "inhibit" includes its generally accepted meaning which includes prohibiting, preventing, restraining, and slowing, stopping, or reversing progression, severity, or ameliorating a resultant symptom or effect.

Preferred embodiments of the current invention are 2-(3-methoxyphenyl)-3-[4-[2-(1-piperidinyl)ethoxy] phenoxybenzo[b]thiophene hydrochloride, for example, where $R^1$, $R^2$, and $R^4$ are hydrogen, $R^3$ is methoxy, n is two, $R^5$ is piperidinyl, and the hydrochloride salt thereof; 2-(3-hydroxyphenyl)-3-[4-[2-(1-piperidinyl) ethoxy] phenoxybenzo[b]thiophene hydrochloride, for example, where $R^1$, $R^2$, and $R^4$ are hydrogen, $R^3$ is hydroxy, n is two, $R^5$ is piperidinyl, and the hydrochloride salt thereof; 2-(3-fluoro-4-methoxyphenyl)-3-(4-[2-(1-piperidinyl)ethoxy] phenoxybenzo[b]thiophene hydrochloride, for example, where $R^1$ and $R^4$ are hydrogen, $R^2$ is methoxy, $R^3$ is fluoro, n is two, $R^5$ is piperidinyl, and the hydrochloride salt thereof; and 2-(3-fluoro-4-hydroxyphenyl)-3-[4-[2-(1-piperidinyl)ethoxy]phenoxybenzo[b]thiophene hydrochloride, for example, where $R^1$ and $R^4$ are hydrogen, $R^2$ is hydroxy, $R^3$ is fluoro, n is two, $R^5$ is piperidinyl, and the hydrochloride salt thereof.

The compounds of formula I are derivatives of benzo[b]thiophene, which is named and numbered according to the Ring Index, The American Chemical Society, as follows:

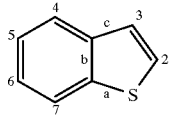

Compounds of formula I in which $R^1$ is —H are prepared via the synthetic route shown below in Scheme I. Using this route, a 3-position leaving group, $R^9$, (where $R^9$ is typically a halogen) is placed on commercially available thianaphthene (formula V) to form a compound of formula VI, which is then coupled with a 4-(protected-hydroxy)phenol, providing compounds of formula VII.

Scheme I

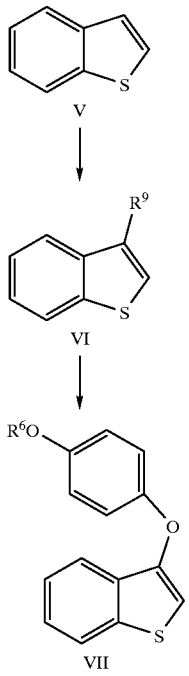

wherein $R^6$ is a hydroxy-protecting group ($R^8$), which can be selectively removed, and $R^9$ is a halogen.

The compound of formula V is commercially available. In the first step of Scheme I, an appropriate leaving group is selectively placed at the 3-position of the formula V starting material via standard procedures. Appropriate $R^9$ leaving groups include the sulfonates such as methanesulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as bromo, chloro, and iodo, and other related leaving groups. However, to insure proper placement of the leaving group, the named halogens are preferred, and bromo is especially preferred.

The present reaction is carried out using standard procedures. For example, when the preferred halogenating agents are used, an equivalent of such a halogenating agent, preferably bromine, is reacted with an equivalent of the formula V substrate, in the presence of a suitable solvent such as, for example, chloroform or acetic acid. The reaction is run at a temperature from about 40° C. to about 80° C. The reaction may be monitored by conventional means, such as, for example, thin layer chromatography, to determine completion of the reaction, which is normally complete within six to forty-eight hours.

The reaction product from the above process step, a compound of formula VI, is then reacted with a 4-(protected-hydroxy)phenol to form compounds of formula VII in which $R^6$ is a selectively removable hydroxy-protecting group ($R^8$). Generally, the 4-hydroxy-protecting moiety of the phenol may be any known protecting group which can be selectively removed without removing, when present, the $R^7$ moiety of a formula IIa compound. Preferred $R^6$ protecting groups include methoxymethyl, 4-methoxybenzyl, and benzyl. Of these, benzyl is especially preferred. The 4-(protected-hydroxy)phenol reactants are commercially available or can be prepared via standard procedures.

This coupling reaction to form compounds of formula VII is known in the art as an Ullman reaction and is run according to standard procedures [see, e.g., *Advanced Organic Chemistry: Reactions, Mechanisms, and Structure*, Fourth Edition, 3–16, (J. March, ed., John Wiley & Sons, Inc. 1992); Jones, C. D., *J. Chem. Soc. Perk. Trans. I*, 4:407 (1992)].

In general, equivalent amounts of the two aryl substrates, in the presence of up to an equimolar amount of a copper(I) oxide catalyst and an appropriate solvent, are heated to reflux under an inert atmosphere. Preferably, an equivalent of a formula VI compound in which $R^9$ is bromo is reacted with an equivalent amount of 4-benzyloxyphenol in the presence of an equivalent of cuprous oxide.

Appropriate solvents for this reaction are those solvents or mixture of solvents which remain inert throughout the reaction. Typically, organic bases, particularly a hindered base, such as, for example, 2,4,6-collidine, are the preferred solvents.

The temperature employed in this step should be sufficient to effect completion of this coupling reaction, and will influence the amount of time required therefor. When the reaction mixture is heated to reflux under an inert atmosphere such as nitrogen, the time-to-completion usually will be from about 20 to about 60 hours.

Compounds of formula VII are then arylated in the 2-position via Suzuki coupling [see, e.g., Suzuki, A., *Pure and Appl. Chem.*, 6(2):213–222 (1994)]. Using one Suzuki coupling option, a formula VII compound is selectively halogenated at the 2-position (VIIIa), and then coupled with an arylboronic acid compound of formula IXa (Scheme II, Route A).

Preferably, however, an arylboronic acid of formula VIIIb is formed from a compound of formula VII, and then reacted with a halo-arene of formula IXb to give intermediates of formula IIa (Scheme II, Route B). Such intermediates (IIa) are useful for preparing pharmaceutically active compounds of the present invention (formula Ia compounds).

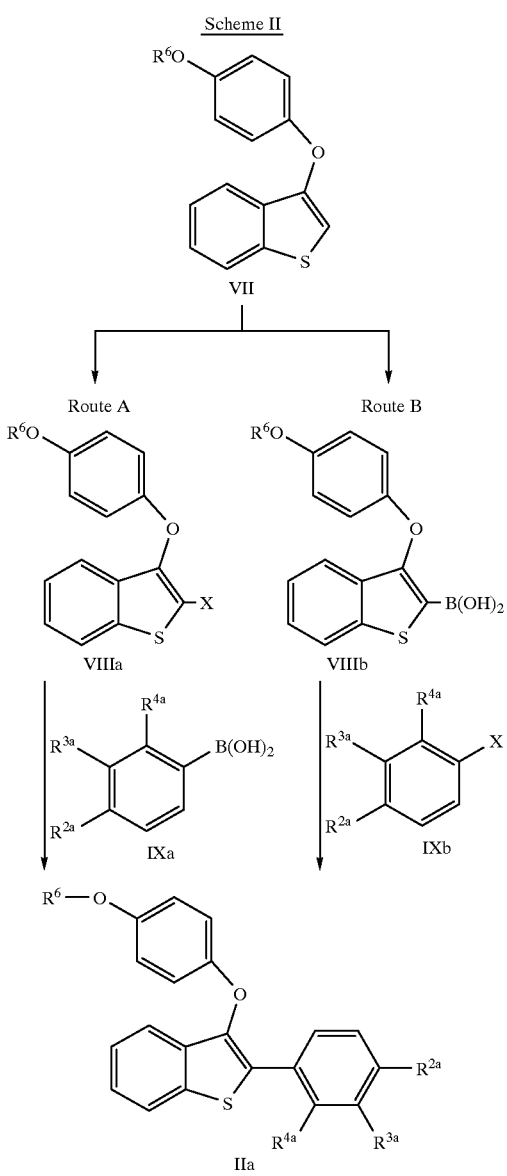

wherein:

$R^{2a}$, $R^{3a}$, $R^{4a}$, and $R^6$ have their previous meanings, with the proviso that $R^{3a}$ and $R^{4a}$ are not both hydrogen; and X is a halogen.

The first step in Route A in Scheme II is the 2-position iodination or bromination of a formula VII compound using standard procedures. Generally, a formula VII compound is reacted with a slight excess of n-butyllithium in hexane, in an appropriate solvent and under an inert atmosphere such as nitrogen, followed by the dropwise addition of a slight excess of the desired halogenating agent in an appropriate solvent. Preferably the halogenating agent for this step is iodine. However, the use of bromine, such as, for example, N-bromosuccinimide, is sufficient.

Appropriate solvents include an inert solvent or mixture of solvents such as, for example, diethyl ether, dioxane, and tetrahydrofuran (THF). Of these, tetrahydrofuran, particularly anhydrous THF, is preferred.

The present selective, 2-position halogenation reaction is optionally run at a temperature from about –75° C. to about 85° C.

The product of the above reaction, a halo-arene of formula VIIIa, is then coupled with an arylboronic acid of formula IXa, via standard Suzuki coupling procedures, to provide compounds of formula IIa. Compounds of formula IXa, in which $R^6$ is —$OR^8$ ($R^8$ is a hydroxy-protecting group as defined, supra) are derived from commercially available compounds via procedures well known to one of ordinary skill in the art (see, e.g., March J.; and Suzuki, A., supra).

In the present coupling reaction, a slight excess of a formula IXa compound is reacted with each equivalent of a formula VIIIa compound in the presence of a palladium catalyst and an appropriate base in an inert solvent, such as toluene.

Although various palladium catalysts drive Suzuki coupling reactions, the catalyst selected is usually reaction-specific. The use of a tetrakis triphenylphosphine palladium catalyst in the present reaction is a preferred catalyst.

Likewise, various bases may be used in the present coupling reaction. However, it is preferred to use an alkali metal carbonate, particularly preferred is 2 N sodium carbonate.

The temperature employed in this step should be sufficient to effect completion of the coupling reaction. Typically, heating the reaction mixture to reflux for a period from about 2 to about 4 hours is adequate.

In Route B of Scheme II, a 2-position arylboronic acid of formula VIIIb is prepared using well known procedures. Generally, a compound of formula VII is treated with a slight excess of n-butyllithium in hexanes, in an appropriate solvent, and under an inert atmosphere, such as nitrogen, following by the dropwise addition of an appropriate trialkylborate.

Appropriate solvents include an inert solvent or mixture of solvents such as, for example, diethyl ether, dioxane, and tetrahydrofuran (THF). THF, particularly anhydrous THF, is preferred. The preferred trialkylborate used in the present reaction is triisopropyl borate.

The product of this reaction, a compound of formula VIIIb, is then reacted with an aryl halide or aryl triflate of formula IXb, via standard Suzuki coupling procedures, to provide compounds of formula IIa. The preferred reaction conditions for the present reaction are as described for the reaction of compounds of formulae VIIIa and IXa, in Scheme II, which also provide compounds of formula IIa.

The compounds of formula IIa can be converted to those of Ia' via two possible routes. In the first route, the hydroxy-protecting group ($R^8$) is removed, and the free phenol (IIa') is alkylated with an aminoalkyl side-chain (X) as shown in Scheme III:

Scheme III

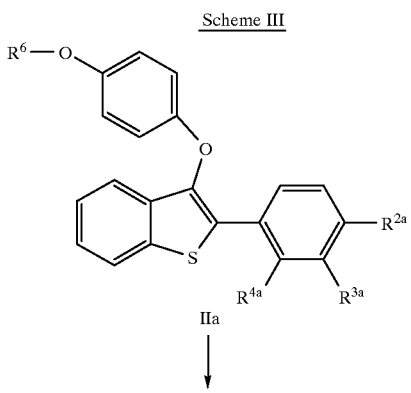

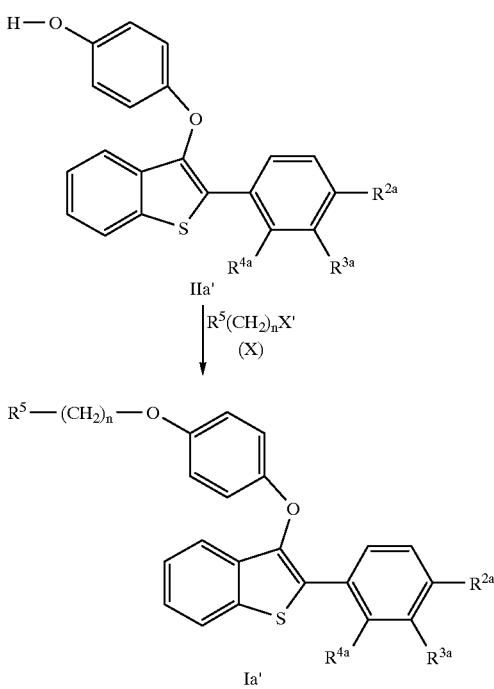

IIa'

↓ R⁵(CH₂)ₙX'
   (X)

Ia' wherein:

$R^{2a}$, $R^{3a}$, $R^{4a}$, and $R^6$ have their previous meanings, with the proviso that $R^{3a}$ and $R^{4a}$ are not both hydrogen; and X' is a halogen.

Alternately, the hydroxy-protecting group ($R^8$) is removed and the free phenol (IIa') is alkylated with an alkyl side-chain (XI) bearing a leaving group, Q, to form a compound of formula IVa. Subsequently, Q is displaced with an amine forming a compound of formula Ia' as shown in Scheme IV:

Scheme IV

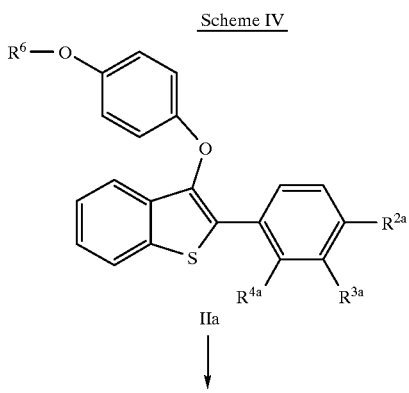

IIa

↓

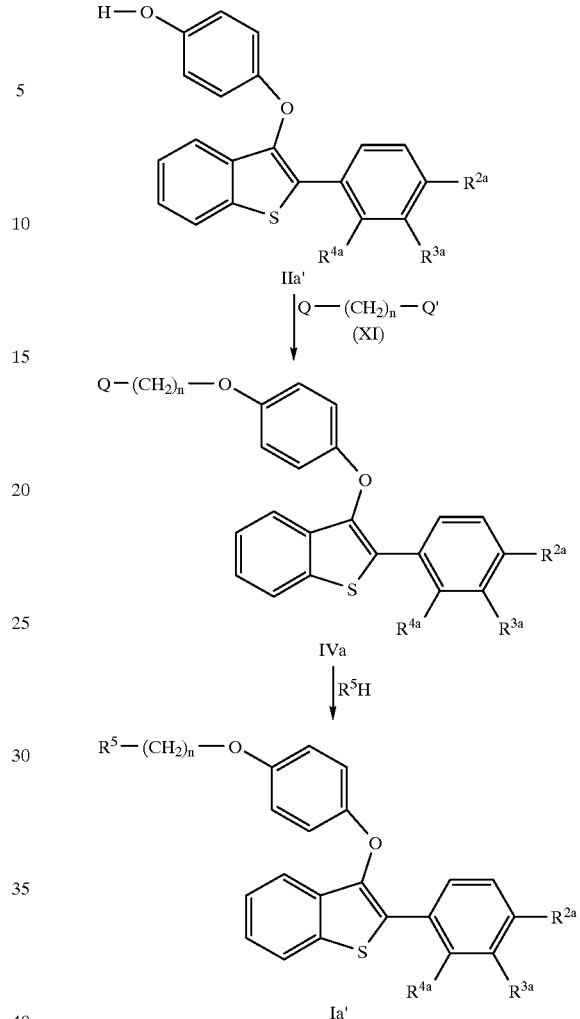

IIa'

↓ Q—(CH₂)ₙ—Q'
   (XI)

IVa

↓ R⁵H

Ia' wherein:
$R^{2a}$, $R^{3a}$, $R^{4a}$, $R^5$ and $R^6$ and n have their previous meanings, with the proviso that $R^{3a}$ and $R^{4a}$ are not both hydrogen; and Q and Q' are both leaving groups.

Following coupling, which forms a formula IIa compound, formula IIa' compounds are prepared by selectively removing the $R^8$ hydroxy-protecting group of a formula IIa compound via well known reduction procedures. It is imperative that the selected procedure will not affect $R^7$ when present (the hydroxy-protecting groups).

When $R^8$ is the preferred benzyl moiety, and $R^7$, when present, is methyl, the present process step is carried out via standard hydrogenolysis procedures. Typically, the formula IIa substrate is added to a suitable solvent or mixture of solvents, followed by the addition of a proton donor to accelerate the reaction and an appropriate hydrogenation catalyst.

Appropriate catalysts include noble metals and oxides such as palladium, platinum, and rhodium oxide on a support such as carbon or calcium carbonate. Of these, palladium-on-carbon, particularly 10% palladium-on-carbon, is the preferred catalyst.

Solvents for this reaction are those solvents or mixture of solvents which remain inert throughout the reaction. Typically, ethylacetate and $C_1$–$C_4$ aliphatic alcohols, particularly ethanol, is preferred.

For the present reaction, hydrochloric acid serves as a preferred proton donor.

The instant reaction is typically run at ambient temperature, using a pressure ranging from about 30 psi to about 50 psi. Progress of this reaction may additionally be monitored by standard chromatographic techniques, such as thin layer chromatography.

In the second step of the process shown in Scheme III, the alkylation of the 4-phenol is carried out via standard procedures. Compounds of formula X are commercially available, or are prepared by means well known to one of ordinary skill in the art. Preferably, the hydrochloride salt of a formula X compound, particularly 2-chloroethylpiperidine hydrochloride, is used.

$$R^5\text{—}(CH_2)\text{—}Cl\ (Br) \qquad\qquad X$$

wherein $R_5$ is as previously defined.

Generally, at least about 1 equivalent of formula IIa' substrate are reacted with 2 equivalents of a formula X compound in the presence of at least about 4 equivalents of an alkali metal carbonate, preferably cesium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Typically, ambient temperature is sufficient and preferred.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative method for preparing compounds of formula Ia', a formula IIa' compound is reacted with an excess of an alkylating agent of the formula XI in the presence of alkaline base, $$Q\text{—}(CH_2)_n\text{—}Q' \qquad\qquad XI$$

wherein Q and Q' each are the same or different leaving group, in an alkali solution. Appropriate leaving groups would be choro, bromo, tosylates, myslates, and the like. Preferred compounds would be where both Q and Q' are bromo.

A preferred alkaline base solution for this alkylation reaction contains potassium carbonate, cesium carbonate, sodium carbonate, and the like, in an inert solvent such as, for example, methyethyl ketone (MEK) or DMF. In this solution, the 4-hydroxy group of the phenyloxy moiety of a formula IIa' compound exists as a phenoxide ion, which displaces one of the leaving groups of the alkylating agent (XI).

This reaction is most favorable when the alkali solution containing the reactants and reagents is brought to reflux and allowed to run to completion. When using MEK as the preferred solvent, reaction times run from about 6 hours to about 20 hours.

The products of this first step are compounds of formula IVa, which are then reacted with $R^5H$, for example, 1-piperidine, 1-pyrrolidine, methyl-1-pyrrolidine, dimethyl-1-pyrrolidine, 4-morpholine, dimethylamine, diethylamine, diisopropylamine, or 1-hexamethyleneimine, via standard techniques, to form compounds of formula Ia'. Preferably, the hydrochloride salt of piperidine is reacted with the alkylated compound of formula IVa in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run for completion. Of course, the progress of this reaction step can be monitored via standard chromatographic techniques.

The compounds of formula Ia' may be converted to other derivatives (Ia), for example, acyl and sulfonyl derivatives of phenolic moieties, by deprotecting, for example, removing $R^7$ groups to form the desired phenols, and then acylating or sulfonating these compounds, as is provided below in Scheme V:

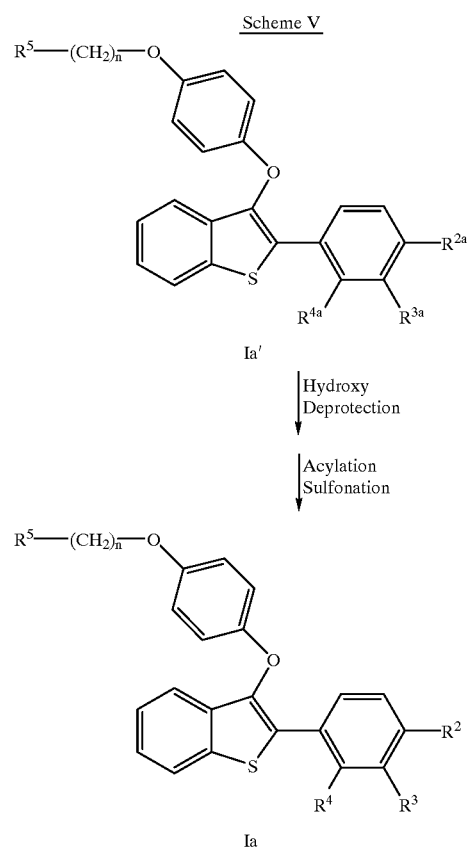

wherein:
$R^{2a}$, $R^{3a}$, $R^{4a}$, $R^2$, $R^3$, $R^4$, and $R^5$, and n have their previous meanings, with the provisos that $R^{3a}$ and $R^{4a}$ are not both hydrogen, and $R^3$ and $R^4$ are not both hydrogen.

Other compounds of formula Ia are obtained by cleaving the $R^7$ hydroxy-protecting group, when present, of formula Ia' compounds using well known procedures. Numerous reactions for the formation and removal of such protecting groups are described in a number of standard works including, for example, *Protective Groups in Organic*

Chemistry, Plenum Press (London and New York, 1973); Green, T. W., Protective Groups in Organic Synthesis, Wiley, (New York, 1981); and The Peptides, Vol. I, Schrooder and Lubke, Academic Press (London and New York, 1965). Methods for removing preferred $R^7$ and/or $R^8$ hydroxy-protecting groups, particularly methyl and methoxymethyl, are essentially as described in the Examples, infra.

Acyl and sulfonyl compounds of formula Ia are prepared by replacing 2', 3', and/or 4'-position hydroxy moieties, when present, with a moiety of the formula —O—CO—($C_1$-$C_6$ alkyl), —OCAr, where Ar is phenyl or substituted phenyl, —O(CO)O($C_1$-$C_6$ alkyl) or —O—$SO_2$—($C_2$-$C_6$ alkyl) via well known procedures. Such methods are described in U.S. Pat. Nos. 5,393,763 and 5,482,949, the disclosures of which are herein incorporated by reference.

For example, when an —O—CO($C_1$-$C_6$ alkyl) group is desired, a mono-, di-, or trihydroxy compound of formula Ia is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., Tetrahedron, 36:2409–2433 (1980).

The present reactions are carried out at moderate temperatures, in the range of from about −25° C. to about 100° C., generally under an inert atmosphere, such as nitrogen gas. However, ambient temperature is usually adequate for the reaction to run.

Acylation of a 2', 3', and/or 4'-position hydroxy groups also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^2$, $R^3$, and/or $R^4$ groups of formula Ia compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, Bull. Chem. Soc. Japan, 38:1979 (1965), and Chem. Ber., 788 and 2024 (1970).

Each of the above techniques which provide —O—CO—($C_1$-$C_6$ alkyl) moieties are carried out in solvents as discussed above. Those techniques which do not produce an acid product in the course of the reaction, of course, do not call for the use of an acid scavenger in the reaction mixture.

When a formula Ia compound is desired in which the 2', 3', and/or 4'-position hydroxy group of a formula I compound is converted to a group of the formula —O—$SO_2$—($C_4$-$C_6$ alkyl), the mono-, di-, or trihydroxy compound is reacted with, for example, a sulfonic anhydride or a derivative of the appropriate sulfonic acid such as a sulfonyl chloride, bromide, or sulfonyl ammonium salt, as taught by King and Monoir, J. Am. Chem. Soc., 97:2566–2567 (1975). The hydroxy compounds also can be reacted with the appropriate sulfonic anhydride or mixed sulfonic anhydrides. Such reactions are carried out under conditions such as were explained above in the discussion of reaction with acid halides, and the like.

Another chemical process may be employed in the preparation of compounds of formula I, and is the preferred process when $R^1$ is not hydrogen. This process utilizes intermediates of formula III

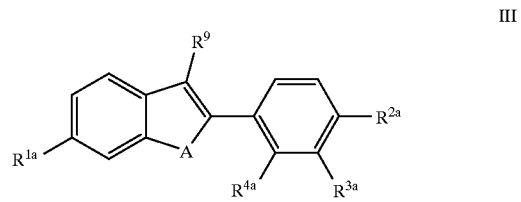

wherein:

$R^{1a}$, $R^{2a}$, $R^{3a}$, and $R^{4a}$ have their previous meanings, with the proviso that $R^{3a}$ and $R^{4a}$ are not both hydrogen; and $R^9$ is a halogen.

Compounds of formula III may be synthesized by variations of several known routes. First, the compounds of formula III made be prepared by a variation of the chemical synthesis which is described in U.S. Pat. Nos. 4,133,814, 4,418,068, and 4,358,593, each of which is herein incorporated by reference. It would be appreciated and apparent to those skilled in the art of organic chemistry as to the necessary modifications in the references, supra, to prepare those intermediates for the synthesis of the compounds of formula III. In brief, a substituted phenyl thiophenol (XII) is condensed with substituted phenacyl halide (XIII), preferred would be the phenacyl bromide, to form an intermediate diaryl-keto-sulfide of formula XIV. This intermediate is cyclized and rearranged to form the compounds of IIIa. This chemical sequence is illustrated in Scheme VI, below.

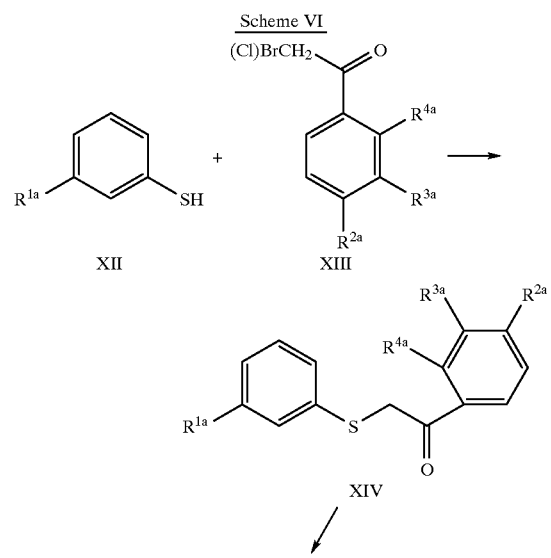

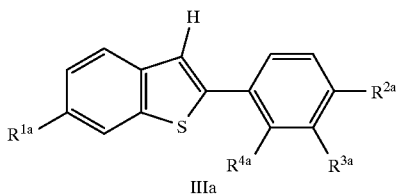

IIIa wherein:
$R^{1a}$, $R^{2a}$, $R^{3a}$, and $R^{4a}$ have their previous meanings with the proviso that $R^{3a}$ and $R^{4a}$ are not both hydrogen.

A second method for the synthesis of compounds IIIa would involve a variation of the Suzuki coupling discussed herein,supra. This chemistry is also taught in U.S. Ser. No. 08/415,014, filed Mar. 31, 1995, the disclosure of which is herein incorporated by reference. This coupling reaction may be executed by two different routes, which are shown in Scheme VII, below. Briefly, a 2-boronic acid thianaphthalene (XV) may be condensed with a halo-sustituted phenyl (XVI) (the iodo-substituted phenyl is preferred) as shown in Route A. Alternatively, a 2-halo thianaphthalene (XVII) (the 2-iodo is preferred) is condensed with a substituted phenylboronic acid (XVIII), as shown in Route B.

of compounds of formula IIIb would be those where $R^9$ is bromo. These compounds may be synthesized by the methods described for the conversion of compounds V to VI in Scheme I, supra. This chemical synthesis is illustrated in Scheme VIII, below.

Scheme VIII

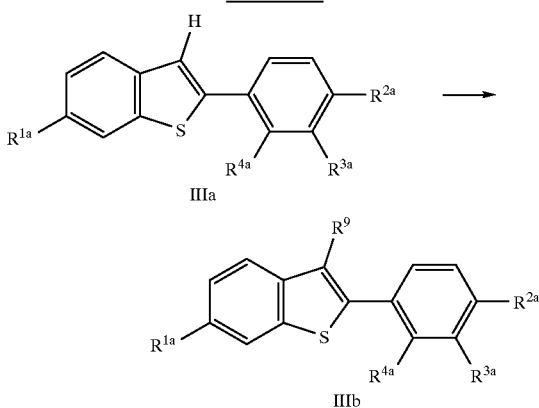

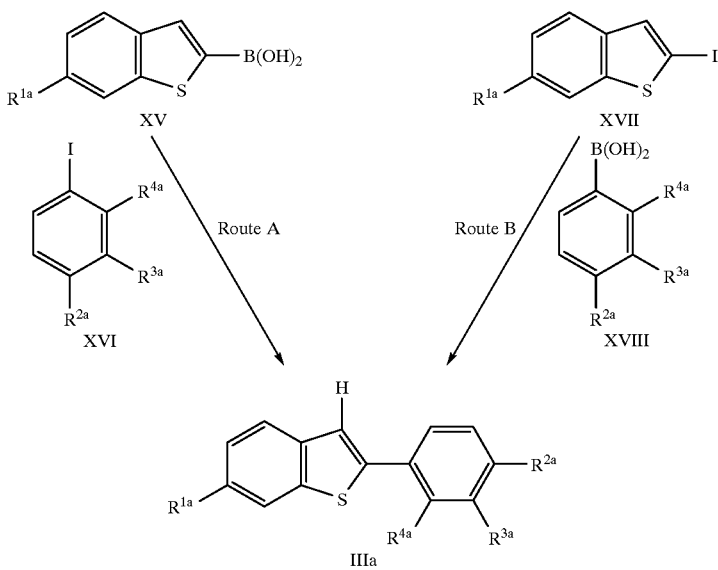

wherein:
$R^{1a}$, $R^{2a}$, $R^{3a}$, and $R^{4a}$ have their previous meanings, with the proviso that $R^{3a}$ and $R^{4a}$ are not both hydrogen.

It would be apparent to those skilled in the art of organic chemistry that there would be cases in the synthesis of compounds of formula IIIa, where one or the other of the schemes desribed, supra, would be preferred. For example, in a case where $R^{2a}$, $R^{3a}$, or $R^{4a}$ is displaceable halogen, then the chemistry of Scheme VII would not be preferred, as one skilled in the art would expect a significant level of undesirable by-products from using this chemistry. However, one or both of the above schemes (VI or VII) would provide for the synthesis of all of the compounds of formula IIIa.

The compounds of formula IIIa may be converted to the compounds of IIIb, where $R^9$ is a halogen. A preferred group wherein:

$R^{1a}$, $R^{2a}$, $R^{3a}$, and $R^{4a}$ have their previous meaning with the proviso that $R^{3a}$ and $R^{4a}$ are not both hydrogen; and $R^9$ is a halogen.

Also, the compounds of formula IIIb may be converted to those of IIIc by oxidation of the sulfur of the benzo[b] thiophene to the sulfoxide. This process is described in co-pending application Ser. No. 08/552,679, (EP 96301304.0, published Sep. 4, 1996) which is a continuation-in-part of U.S. Pat. No. 5,510,357, the disclosures of which are herein incorporated by reference. This is further illustrated in Scheme IX, below.

Scheme IX

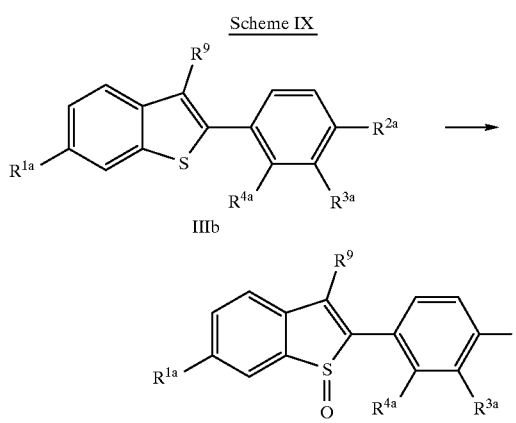

wherein:

$R^{1a}$, $R^{2a}$, $R^{3a}$, and $R^{4a}$ have their previous meaning with the proviso that $R^{3a}$ and $R^{4a}$ are not both hydrogen; and $R^9$ is a halogen.

Either a compound of IIIb or IIIc may be converted to a compound of IIb via the chemistry described in Scheme I, supra. A preferred reactant for this synthetic sequence would be 4-benzyloxyphenol (XX). In the case where the starting material is a compound of formula IIIc, the intermediate compound XIX may be reduced to a compound of IIb by a reduction, which is described fully in the references provided, supra. This synthetic sequence is illustrated in Scheme X, below.

$R^8$ is a hydroxy-protecting group; and $R^9$ is a halogen.

Compounds of IIb are further converted to compounds IIb' by removing $R^8$ to generate the phenol. In the preferred case, where $R^8$ is benzyl, this removal is as described in Scheme III, supra.

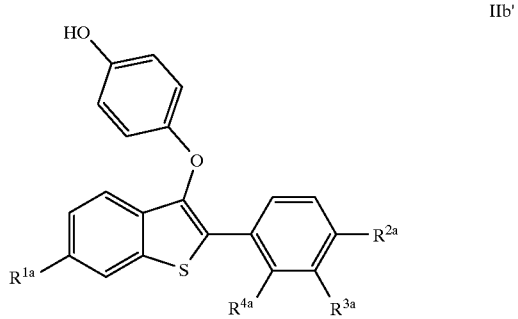

wherein:

$R^{1a}$, $R^{2a}$, $R^{3a}$, and $R^{4a}$ have their previous meaning with the proviso that $R^{3a}$ and $R^{4a}$ are not both hydrogen.

Compounds of formula IIb' are further converted to either Ib or IVb by O-alkylation of the free phenol. Compounds of IIb' are converted to Ib by alkylation with a compound of formula X as described in Scheme III, supra.

Alternately, a compound of IIb' may be alkylated with a compound of formula XI to form a compound of formula IVb via the chemistry described in Scheme IV, supra.

Scheme X

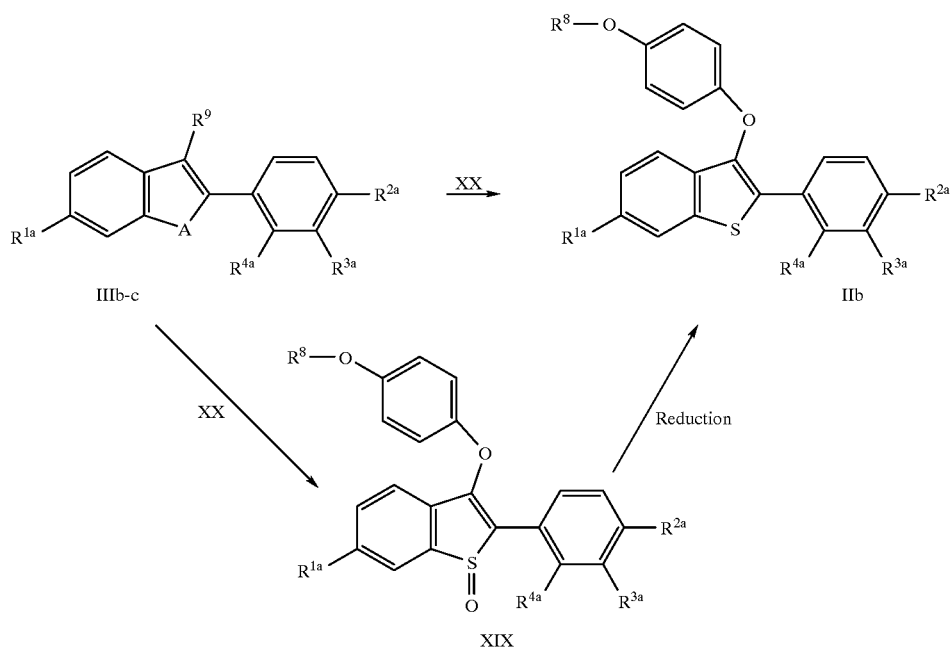

wherein:

$R^{1a}$, $R^{2a}$, $R^{3a}$, $R^{4a}$, and A have their previous meanings, with the proviso that $R^{3a}$ and $R^{4a}$ are not both hydrogen;

Subsequently, formula IVb compounds are converted to compounds of Ib by displacement of the leaving group Q with an amine, $R^5H$, as described in Scheme IV, supra. This chemistry is further described in Scheme XI, below.

Scheme XI

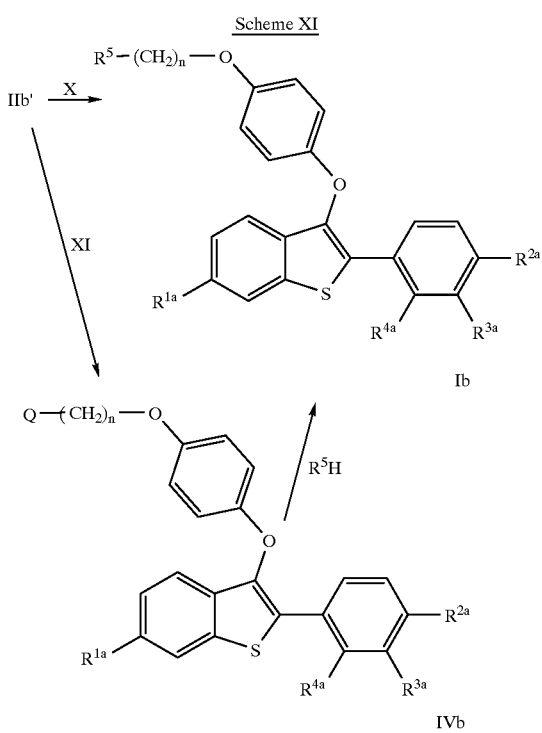

wherein:
$R^{1a}$, $R^{2a}$, $R^{3a}$, $R^{4a}$, and $R^5$ and n have their previous meanings, with the proviso that $R^{3a}$ and $R^{4a}$ are not both hydrogen; and Q is a leaving group.

The compounds of formula Ib may be converted to other compounds of formula I by removal of the hydroxy-protecting groups (—$OR^7$) on $R^{2a}$, $R^{3a}$, or $R^{4a}$, when present, to form the free phenols. This chemistry is discussed herein, supra. The free phenols may be acylated or sulfonated with appropriate agents. This chemistry is also discussed herein, supra.

The compounds of formula I include the compounds of formula Ia, Ia', and Ib. The compounds of formula I include, but are not limited to:

2-(3-methoxyphenyl)-3-[4-[2-(1-piperidinyl)ethoxy]phenoxy]-6-hydroxybenzo[b]thiophene;
2-(3-methoxyphenyl)-3-[4-[2-(1-piperidinyl)ethoxy]phenoxy]-6-hydroxybenzo[b]thiophene hydrochloride;
2-(3-hydroxyphenyl)-3-[4-[2-(1-piperidinyl)ethoxy]phenoxy]-6-hydroxybenzo[b]thiophene;
2-(3-hydroxyphenyl)-3-[4-[2-(1-piperidinyl)ethoxy]phenoxy]-6-hydroxybenzo[b]thiophene hydrochloride;
2-(3-hydroxyphenyl)-3-[4-[2-(1-piperidinyl)ethoxy]phenoxy]-6-methoxybenzo[b]thiophene;
2-(3-hydroxyphenyl)-3-[4-[2-(1-piperidinyl)ethoxy]phenoxy]-6-methoxybenzo[b]thiophene hydrochloride;
2-(3-methoxyphenyl)-3-[4-[2-(1-piperidinyl)ethoxy]phenoxy]benzo[b]thiophene;
2-(3-hydroxyphenyl)-3-[4-[2-(1-piperidinyl)ethoxy]phenoxy]benzo[b]thiophene;
2-(3-hydroxyphenyl)-3-[4-[2-(1-piperidinyl)ethoxy]phenoxy]benzo[b]thiophene hydrochloride;
2-(3,4-dimethoxyphenyl)-3-[4-[2-(1-piperidinyl)ethoxy]phenoxy]-6-methoxybenzo[b]thiophene;
2-(3,4-dimethoxyphenyl)-3-[4-[2-(1-piperidinyl)ethoxy]phenoxy]-6-hydroxybenzo[b]thiophene;
2-(3,4-dihydroxyphenyl)-3-[4-[2-(1-piperidinyl)ethoxy]phenoxy]-6-hydroxybenzo[b]thiophene;
2-(3,4-dihydroxyphenyl)-3-[4-[2-(1-piperidinyl)ethoxy]phenoxy]-6-methoxybenzo[b]thiophene;
2-(3-methoxy-4-fluorophenyl)-3-[4-[2-(1-piperidinyl)ethoxy]phenoxy]-6-hydroxybenzo[b]thiophene;
2-(3-hydroxy-4-fluorophenyl)-3-[4-[2-(1-piperidinyl)ethoxy]phenoxy]-6-hydroxybenzo[b]thiophene;
2-(2-methyl-3-hydroxyphenyl)-3-[4-[2-(1-piperidinyl)ethoxy]phenoxy]-6-hydroxybenzo[b]thiophene;
2-(3-chloro-4-hydroxyphenyl)-3-[4-[2-(1-piperidinyl)ethoxy]phenoxy]-6-hydroxybenzo[b]thiophene;
2-(3-methoxyphenyl)-3-[4-[2-(1-piperidinyl)ethoxy]phenoxy]-6-acetyloxybenzo[b]thiophene;
2-(3-hydroxyphenyl)-3-[4-[2-(1-piperidinyl)ethoxy]phenoxy]-6-benzoyloxybenzo[b]thiophene;
2-(3-n-butylsulfonoyloxyphenyl)-3-[4-[2-(1-piperidinyl)ethoxy]phenoxy]-6-hydroxybenzo[b]thiophene;
2-(2-hydroxy-3-hydroxyphenyl)-3-[4-[2-(1-piperidinyl)ethoxy]phenoxy]-6-hydroxybenzo[b]thiophene;
2-(2-fluoro-3-acetyloxy-4-fluorophenyl)-3-[4-[2-(1-piperidinyl)ethoxy]phenoxy]benzo[b]thiophene citrate;
2-(2-acetyloxy-3-acetyloxyphenyl)-3-[4-[2-(1-piperidinyl)ethoxy]phenoxy]-6-acetyloxybenzo[b]thiophene;
2-(3-methoxyphenyl)-3-[4-[2-(1-pyrrolidinyl)ethoxy]phenoxy]-6-hydroxybenzo[b]thiophene oxalate;
2-(3-methoxyphenyl)-3-[4-[3-(1-piperidinyl)propoxy]phenoxy]benzo[b]thiophene;
2-(3-hydroxyphenyl)-3-[4-[3-(1-hexamethylenimino)propoxy]phenoxy]-6-hydroxybenzo[b]thiophene;
2-(3-hydroxyphenyl)-3-[4-[2-(1-pyrrolidinyl)ethoxy]phenoxy]-6-hydroxybenzo[b]thiophene hydrochloride;
2-(3-hydroxyphenyl)-3-[4-[2-(1-hexamethyleneimino)ethoxy]phenoxy]-6-hydroxybenzo[b]thiophene;
2-(3,4-dihydroxyphenyl)-3-[4-[3-(1-hexamethyleneimino)propopoxy]phenoxy]-6-hydroxybenzo[b]thiophene; and
2-(2-methyl-3-hydroxyphenyl)-3-[4-[2-(1-pyrrolidinyl)ethoxy]phenoxy]-6-hydroxybenzo[b]thiophene.

The compounds of formula II include the compounds of formula IIa, IIa', and IIb. The compounds of formula II include, but are not limited to:

2-(3-methoxyphenyl)-3-(4-benzyloxyphenoxy)-6-methoxybenzo[b]thiophene;
2-(3-methoxyphenyl)-3-(4-hydroxyphenoxy)-6-methoxybenzo[b]thiophene;
2-(3-methoxyphenyl)-3-(4-benzyloxyphenoxy)benzo[b]thiophene;
2-(3-methoxyphenyl)-3-(4-hydroxyphenoxy)benzo[b]thiophene;
2-(3-methoxy-4-fluorophenyl)-3-(4-benzyloxyphenoxy)-6-methoxybenzo[b]thiophene;
2-(3-methoxy-4-fluorophenyl)-3-(4-hydroxyphenoxy)-6-methoxybenzo[b]thiophene;
2-(2-methoxyphenyl)-3-(4-benzyloxyphenoxy)-6-methoxybenzo[b]thiophene;
2-(2-methoxyphenyl)-3-(4-hydroxyphenoxy)-6-methoxybenzo[b]thiophene;
2-(3-methoxyphenyl)-3-(4-hydroxyphenoxy)-6-methoxybenzo[b]thiophene;
2-(3-methoxy-4-fluorophenyl)-3-(4-benzyloxyphenoxy)benzo[b]thiophene;
2-(3-methoxy-4-fluorophenyl)-3-(4-hydroxyphenoxy)benzo[b]thiophene;
2-(2-cloro-3-methoxy-4-methoxyphenyl)-3-(4-benzyloxyphenoxy)-6-methoxybenzo[b]thiophene; and
2-(2-cloro-3-methoxy-4-methoxyphenyl)-3-(4-hydroxyphenoxy)-6-methoxybenzo[b]thiophene.

The compounds of formula III include the compounds of formula IIIa, IIIb, and IIIc. The compounds of formula III include, but are not be limited to:

2-(3-methoxyphenyl)-3-(4-benzyloxyphenoxy)-6-methoxybenzo[b]thiophene;
2-(3-methoxyphenyl)-6-methoxybenzo[b]thiophene;
2-(3-methoxyphenyl)-3-bromo-6-methoxybenzo[b]thiophene;
2-(3-methoxyphenyl)-3-tosyl-6-methoxybenzo[b]thiophene;
2-(3-methoxyphenyl)-3-chloro-6-methoxybenzo[b]thiophene;
2-(3-methoxyphenyl)-6-methoxybenzo[b]thiophene-1-oxide;
2-(3-methoxyphenyl)-3-bromo-6-methoxybenzo[b]thiophene-1-oxide;
2-(2-methoxyphenyl)-3-(4-benzyloxyphenoxy)-6-methoxybenzo[b]thiophene;
2-(2-methoxyphenyl)-6-methoxybenzo[b]thiophene;
2-(2-methoxyphenyl)-3-bromo-6-methoxybenzo[b]thiophene;
2-(2-methoxyphenyl)-3-tosyl-6-methoxybenzo[b]thiophene;
2-(2-methoxyphenyl)-3-chloro-6-methoxybenzo[b]thiophene;
2-(2-methoxyphenyl)-6-methoxybenzo[b]thiophene-1-oxide;
2-(2-methoxyphenyl)-3-bromo-6-methoxybenzo[b]thiophene-1-oxide;
2-(3-methoxy-4-fluorophenyl)-3-(4-benzyloxyphenoxy)-6-methoxybenzo[b]thiophene;
2-(3-methoxy-4-fluorophenyl)-6-methoxybenzo[b]thiophene;
2-(3-methoxy-4-fluorophenyl)-3-bromo-6-methoxybenzo[b]thiophene;
2-(3-methoxy-4-fluorophenyl)-3-tosyl-6-methoxybenzo[b]thiophene;
2-(3-methoxy-4-fluorophenyl)-3-chloro-6-methoxybenzo[b]thiophene;
2-(3-methoxy-4-fluorophenyl)-6-methoxybenzo[b]thiophene-1-oxide;
2-(3-methoxy-4-fluorophenyl)-3-bromo-6-methoxybenzo[b]thiophene-1-oxide;
2-(3-methoxyphenyl)-3-(4-benzyloxyphenoxy)-6-methoxybenzo[b]thiophene;
2-(3-methoxyphenyl)-6-methoxybenzo[b]thiophene;
2-(3-methoxyphenyl)-3-bromo-6-methoxybenzo[b]thiophene;
2-(3-methoxyphenyl)-3-tosyl-6-methoxybenzo[b]thiophene;
2-(3-methoxyphenyl)-3-chloro-6-methoxybenzo[b]thiophene;
2-(3-methoxyphenyl)-6-methoxybenzo[b]thiophene-1-oxide;
2-(3-methoxyphenyl)-3-bromo-6-methoxybenzo[b]thiophene-1-oxide;
2-(3-methoxyphenyl)-3-(4-benzyloxyphenoxy)benzo[b]thiophene;
2-(3-methoxyphenyl)benzo[b]thiophene;
2-(3-methoxyphenyl)-3-bromobenzo[b]thiophene;
2-(3-methoxyphenyl)-3-tosylbenzo[b]thiophene;
2-(3-methoxyphenyl)-3-chlorobenzo[b]thiophene;
2-(3-methoxyphenyl)benzo[b]thiophene-1-oxide;
2-(3-methoxyphenyl)-3-bromobenzo[b]thiophene-1-oxide;

The compounds of formula IV include those of formula IVa and IVb. Compounds of formula IV include, but are not limited to:

2-(3-methoxyphenyl)-3-[4-(2-bromoethoxy)phenoxy]-6-methoxybenzo[b]thiophene;
2-(3-methoxyphenyl)-3-[4-(2-bromopropoxy)phenoxy]-6-methoxybenzo[b]thiophene;
2-(3-methoxyphenyl)-3-[4-(2-chloroethoxy)phenoxy]-6-methoxybenzo[b]thiophene;
2-(3-methoxyphenyl)-3-[4-(2-chloropropoxy)phenoxy]-6-methoxybenzo[b]thiophene;
2-(3-methoxyphenyl)-3-[4-(2-tosylethoxy)phenoxy]-6-methoxybenzo[b]thiophene;
2-(3-methoxyphenyl)-3-[4-(2-bromoethoxy)phenoxy]benzo[b]thiophene;
2-(3-methoxyphenyl)-3-[4-(2-bromopropoxy)phenoxy]benzo[b]thiophene;
2-(3-methoxyphenyl)-3-[4-(2-chloroethoxy)phenoxy]benzo[b]thiophene;
2-(3-methoxyphenyl)-3-[4-(2-chloropropoxy)phenoxy]benzo[b]thiophene;
2-(3-methoxyphenyl)-3-[4-(2-tosylethoxy)phenoxy]benzo[b]thiophene;
2-(3-methoxy-4-fluorophenyl)-3-[4-(2-bromoethoxy)phenoxy]-6-methoxybenzo[b]thiophene;
2-(3-methoxy-4-fluorophenyl)-3-[4-(2-bromopropoxy)phenoxy]-6-methoxybenzo[b]thiophene;
2-(3-methoxy-4-fluorophenyl)-3-[4-(2-chloroethoxy)phenoxy]-6-methoxybenzo[b]thiophene;
2-(3-methoxy-4-fluorophenyl)-3-[4-(2-chloropropoxy)phenoxy]-6-methoxybenzo[b]thiophene;
2-(3-methoxy-4-fluorophenyl)-3-[4-(2-tosylethoxy)phenoxy]-6-methoxybenzo[b]thiophene;
2-(2-methoxyphenyl)-3-[4-(2-bromoethoxy)phenoxy]-6-methoxybenzo[b]thiophene;
2-(2-methoxyphenyl)-3-[4-(2-bromopropoxy)phenoxy]-6-methoxybenzo[b]thiophene;
2-(2-methoxyphenyl)-3-[4-(2-chloroethoxy)phenoxy]-6-methoxybenzo[b]thiophene;
2-(2-methoxyphenyl)-3-[4-(2-chloropropoxy)phenoxy]-6-methoxybenzo[b]thiophene; and
2-(2-methoxyphenyl)-3-[4-(2-tosylethoxy)phenoxy]-6-methoxybenzo[b]thiophene.

The term "solvate" represents an aggregate that comprises one or more molecules of the solute, such as a formula I compound, with one or more molecules of solvent. Although the free-base form of formula I compounds can be used in the methods of the present invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The present invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the present invention which is capable of inhibiting, alleviating, ameliorating, treating, or preventing further symptoms in mammals, including humans, suffering from estrogen deprivation, for example, menopause or ovariectomy, or inappropriate estrogen stimulation such as uterine fibrosis or endometriosis, or suffering from aortal smooth muscle cell profileration or restenosis. In the case of estrogen-dependent cancers, the term "effective amount" means the amount of compound of the present invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 100 mg, and more typically from 15 mg to 80 mg. Such dosages will be administered to a patient in need of treatment from one to three times each day or as often as needed for efficacy, normally for at least six months.

The present invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed infra. The present invention contemplates and encompasses such maladies although not specified by name.

Compounds of the current invention may also be used in conjunction with other mixed estrogen agonists/antagonists, especially those which demonstrate increased detrimental stimulation of uterine tissue, such as, for example, tamoxifene, droloxifene, nafoxidene, or clomiphene.

As a further embodiment of the invention, the compounds of formula I may be administered along with an effective amount of an additional therapeutic agent, including but not limited to estrogen, progestin, other benzothiophene compounds including raloxifene, bisphosphonate compounds such as alendronate and tiludronate, parathyroid hormone (PTH), including truncated and/or recombinant forms of PTH such as, for example, PTH (1-34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-α-ethynyl estradiol (0.01–0.03 mg/day), mestranol (0.05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are preferred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
| --- | --- |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension
Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following examples and preparations are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

NMR data for the following Examples were generated on a GE 300 MHz NMR instrument, and anhydrous d-6 DMSO was used as the solvent unless otherwise indicated.

Preparation 1

3-(4-Benzyloxyphenoxy)benzo[b]thiophene

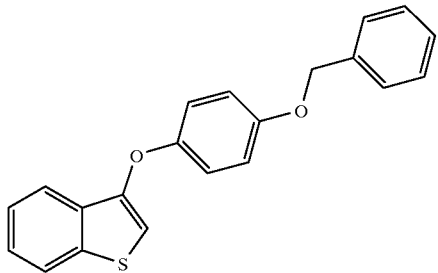

To a solution of 3-bromo-benzo[b]thiophene (69.62 g, 0.325 mol) in 55 mL of anhydrous collidine under $N_2$ was added 4-benzyloxyphenol (97.6 g, 0.488 mol) and cuprous oxide (23.3 g, 0.163 mol). The mixture was heated to reflux for 24 hours. Upon cooling, the reaction mixture was diluted with ethyl acetate (200 mL) and the crude mixture filtered through a pad of Celite® (Aldrich, Milwaukee, Wis.) to remove inorganic salts. The filtrate was washed with 1 N hydrochloric acid (3×150 mL). The organic was dried with sodium sulfate and concentrated in vacuo to a liquid. Thianaphthene was removed by distillation (10 mm Hg, 115–120° C.). The remainder of the material was chromatographed (silicon dioxide, hexanes: ethyl acetate 85:15) to provide 12.2 g of benzo[b]thiophene and 12.95 g (35% based on recovered starting material) of 3-(4-benzyloxyphenoxy)benzo[b]thiophene as an off-white solid.

mp 84–86° C. $^1$H NMR (CDCl$_3$) d 7.91–7.83 (m, 2H), 7.47–7.34 (m, 7H), 7.04 (q, $J_{AB}$=9.0 Hz, 4H), 6.47 (s, 1H), 5.07 (s, 2H). Anal. Calcd. for $C_{21}H_{16}O_2S$: C, 75.88; H, 4.85. Found: C, 75.75; H, 5.00.

Preparation 2

2-Iodo-3-(4-benzyloxyphenoxy)benzo[b]thiophene

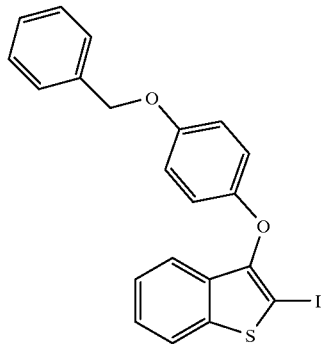

To a solution of 3-(4-benzyloxyphenoxy)benzo[b]thiophene (6.00 g, 18.1 mmol) in anhydrous tetrahydrofuran (100 mL) under $N_2$ at −78° C. was added n-butyllithium (12.4 mL, 19.9 mmol, 1.6 M in hexanes) dropwise via syringe. The solution turned from colorless to deep orange. After stirring for 20 minutes at −78° C., the lithio species was treated with $I_2$ (5.03, 19.9 mmol), added dropwise via canula as a solution in 50 mL of anhydrous tetrahydrofuran. Upon completion of the addition, the reaction turned light yellow in color, and was allowed to slowly warm to room temperature. The reaction was quenched by the addition of 0.1 N sodium sulfite solution (200 mL). The layers were separated and the aqueous extracted with ethyl acetate (2×150 mL). The organic layers were combined, dried (sodium sulfate), and concentrated in vacuo to give an oil that crystallized on standing. Recrystallization from hexanes/ethyl ether yielded 7.10 g (86%) of 2-iodo-3-(4-benzyloxyphenoxy)benzo[b]thiophene as a white crystalline powder. mp 87–92° C. $^1$H NMR (CDCl$_3$) d 7.72 (d, J=8.1 Hz, 1H), 7.47–7.20 (m, 8H), 6.89 (s, 4H), 5.01 (s, 2H). Anal. Calcd. for $C_{21}H_{15}O_2SI$: C, 55.03; H, 3.30. Found: C, 55.29; H, 3.31.

Preparation 3

2-(3-Methoxyphenyl)-3-(4-benzyloxyphenoxy)benzo[b]thiophene

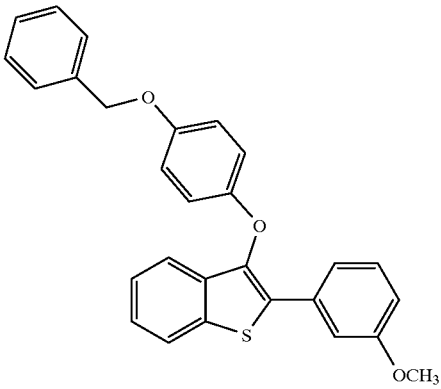

To a solution of 2-iodo-3-(4-benzyloxyphenoxy)benzo[b]thiophene (5.00 g, 11.0 mmol) in 50 mL of toluene under $N_2$ were added 3-methoxyphenylboronic acid (2.00 g, 13.0 mmol), $(Ph_3P)_4Pd$ (0.75 g, 0.66 mmol), and 18.0 mL of 2.0 N $Na_2CO_3$ solution. The resulting mixture was heated to reflux for 2 h. Upon cooling to room temperature, the reaction was diluted with EtOAc and extracted several times with 0.1 N NaOH. The organic was then dried ($Na_2SO_4$) and concentrated in vacuo to an oil. Chromatography ($SiO_2$, 0–10% $Et_2O$/hexanes) provided 4.8 g (99%) of 2-(3-methoxyphenyl)-3-(4-benzyloxyphenoxy)benzo[b]thiophene as a brown oil.

$^1$H NMR (CDCl$_3$) d 7.79 (d, J=8.0 Hz, 1H), 7.46–7.27 (m, 11H), 6.94–6.85 (m, 5H), 5.00 (s, 2H), 3.76 (s, 3H). FD mass spec: 438. Anal. Calcd. for $C_{28}H_{22}O_3S$: C, 76.69; H, 5.06. Found: C, 76.74; H, 5.15.

Preparation 4

2-(3-Methoxyphenyl)-3-(4-hydroxyphenoxy)benzo[b]thiophene

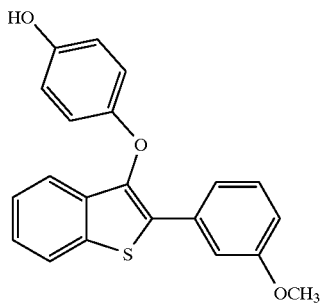

To a solution of 2-(3-methoxyphenyl)-3-(4-benzyloxyphenoxy)benzo[b]thiophene (8.30 g, 29.0 mmol) in 1:1 (100 mL) EtOH/EtOAc in a Paar bottle was added 10% Pd/C (4.0 g). To this suspension was added 2.0 mL of con. HCl. The resulting mixture was hydrogenated at 40 psi for 20 min. The reaction was filtered through Celite®, and the filtrate was concentrated in vacuo to an oil. The crude product was partitioned between $CHCl_3$ and sat. $NaHCO_3$ solution. The layers were separated, and the organic was dried ($Na_2SO_4$) and concentrated in vacuo to give 3.8 g (61%) of 2-(3-methoxyphenyl)-3-(4-hydroxyphenoxy)benzo[b]thiophene as an amber brown foam. $^1$H NMR ($CDCl_3$) d 7.80 (d, J=8.1 Hz, 1H), 7.46–7.27 (m, 6H), 6.88–6.84 (m, 3H), 6.71–6.74 (m, 2H), 4.57 (s, 1H), 3.77 (s, 3H). FD mass spec: 348. Anal. Calcd. for $C_{21}H_{16}O_3S$: C, 72.39; H, 4.63. Found: C, 72.10; H, 4.63.

Example 1

2-(3-Methoxyphenyl)3-[4-[2-(1-piperidinyl)ethoxy]phenoxy]benzo[b]thiophene Hydrochloride

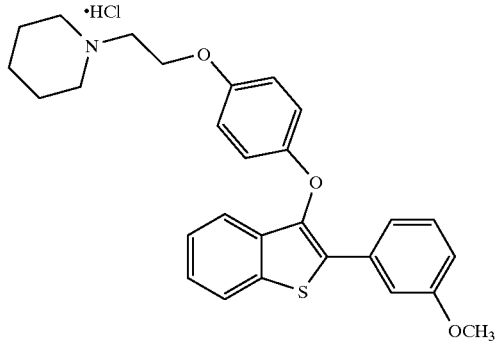

To a solution of 2-(3-methoxyphenyl)-3-(4-hydroxyphenoxy)benzo[b]thiophene (3.27 g, 9.40 mmol) in 200 mL of anhydrous DMF was added finely ground anhydrous $K_2CO_3$ (13.0 g, 94 mmol) and 2-chloroethylpiperidine (2.40 g, 14.1 mmol). The resulting solution was stirred under $N_2$ at room temperature for 16 h. The reaction was then partitioned between EtOAc and $H_2O$. The layers were separated and the organic was washed several times with H2O. The organic was dried ($Na_2SO_4$) and concentrated in vacuo to an oil that was chromatographed ($SiO_2$, 0–5% $CH_3OH/CHCl_3$) to provide 3-[4-[2-(1-piperidinyl)ethoxy]phenoxy]-2-(3-methoxyphenyl)benzo[b]thiophene as a brown oil. This material was treated with $Et_2O.HCl$ to provide 2.0 g (43%) 3-[4-[2-(1-piperidinyl)ethoxy]phenoxy]-2-(3-methoxyphenyl)benzo[b]thiophene hydrochloride as a white solid.

mp 184–185° C. $^1$H NMR ($CDCl_3$) d 7.79 (d, J=7.8 Hz, 1H), 7.42–7.25 (m, 7H), 6.92–6.77 (m, 4H), 4.49 (br s, 2H), 3.78 (s, 3H), 3.65–3.60 (m, 2H), 3.35 (br s, 2H), 2.81–2.77 (m, 2H), 2.30–2.26 (m, 2H), 1.90–1.70 (m, 3H), 1.34 (m, 1H). FD mass spec: 459. Anal. Calcd. for $C_{28}H_{29}NO_3S.1.0$ HCl: C, 67.80; H, 6.10; N, 2.82. Found: C, 67.95; H, 5.99; N, 3.05.

Example 2

2-(3-Hydroxyphenyl)3-[4-[2-(1-piperidinyl)ethoxy]phenoxy]benzo[b]thiophene Hydrochloride

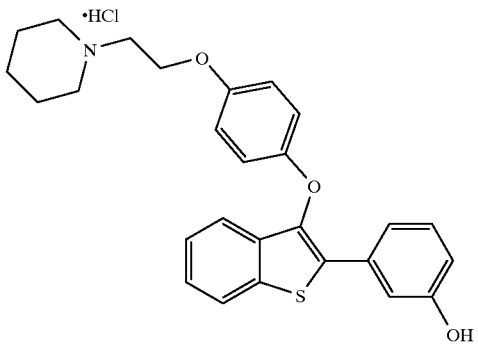

To a solution of 3-[4-[2-(1-piperidinyl)ethoxy]phenoxy]-2-(3-methoxyphenyl)]benzo[b]thiophene hydrochloride (1.14 g, 2.30 mmol) in 100 mL of anhydrous $CH_2Cl_2$ under $N_2$ at 0° C. was added $BBr_3$ (0.54 mL, 5.75 mmol). The resulting dark solution was stirred for 2 h at 0° C. and then poured into a cold, saturated $NaHCO_3$ solution (200 mL). The layers were separated, and the organic was dried ($Na_2SO_4$) and concentrated in vacuo to a tan solid. The free base was dissolved in EtOAc (20 mL) and treated with $Et_2O.HCl$. A white precipitate formed that was collected by vacuum filtration and dried to provide 0.55 g (50%) of 2-(3-hydroxyphenyl)-3-[4-[2-(1-piperidinyl)ethoxy]phenoxy]benzo[b]thiophene hydrochloride as a white solid. mp 195–197° C. $^1$H NMR (DMSO-$d_6$) d 10.29 (br s, 1H), 9.73 (s, 1H), 7.99 (d, J=7.5 Hz, 1H), 7.53–7.35 (m, 3H), 7.35–7.23 (m, 3H), 7.05–6.88 (m, 4H), 6.73 (m, 1H), 4.27 (br s, 2H), 3.45–3.29 (m, 4H), 3.00–2.87 (m, 2H), 1.95–1.70 (m, 5H), 1.03 (m, 1H). FD mass spec: 446. Anal. Calcd. for $C_{27}H_{27}NO_3S.1.0$ HCl: C, 67.28; H, 5.85; N, 2.91. Found: C, 67.18; H, 5.97; N, 2.85.

Preparation 5

2-(3-Fluoro-4-methoxyphenyl)-3-(4-benzyloxyphenoxy)benzo[b]thiophene

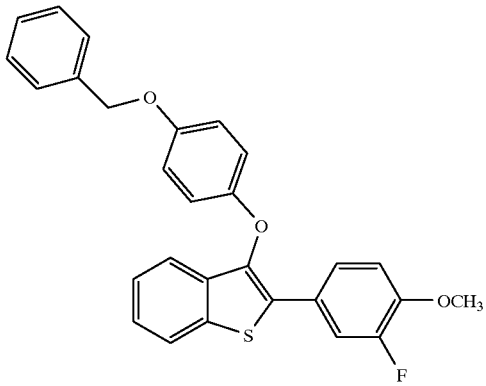

In a manner similar to that used in Preparation 3, the title compound was prepared in 42% yield, and isolated as a yellow solid. mp 122–123° C. $^1$H NMR (CDCl$_3$) d 7.78 (d, J=7.9 Hz, 1H), 7.70–7.60 (m, 2H), 7.43–7.27 (m, 9H), 6.99–6.89 (m, 4H), 5.00 (s, 2H), 3.91 (s, 3H). FD mass spec: 456. Anal. Calcd. for C$_{28}$H$_{21}$NO$_3$FS: C, 73.66; H, 4.64. Found: 73.42; H, 4.69.

Preparation 6

2-(3-Fluoro-4-methoxyphenyl)-3-(4-hydroxyphenoxy)benzo[b]thiophene

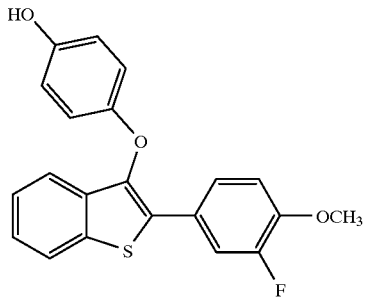

In a manner similar to that used in Preparation 4, the title compound was prepared in 96% yield and isolated as spec: 366. Anal. Calcd. for C$_{21}$H$_{15}$O$_3$SF: C, 68.84; H, 4.13. Found: C, 68,74; H, 4.24.

Example 3

2-(3-Fluoro-4-methoxyphenyl)-3-[4-[2-(1-piperidinyl)ethoxy[phenoxy]benzo[b]thiophene Hydrochloride

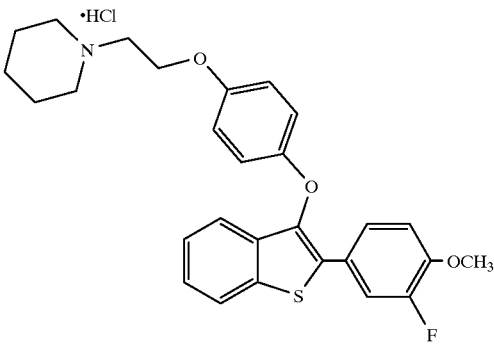

In a manner similar to that used in Example 1, the title compound was prepared in 51% yield and isolated as a white solid. mp 195–197° C. $^1$H NMR (DMSO-d$_6$) d 7.98 (d, J=7.8 Hz, 1H), 7.66–7.46 (m, 2H), 7.66–7.21 (m, 3H), 6.90 (s, 5H), 4.31–4.28 (m, 2H), 3.83 (s, 3H), 3.45–3.38 (m, 4H), 2.96–2.90 (m, 2H), 2.48–2.46 (m, 5H), 1.83 (m, 1H). FD mass spec: 477. Anal. Calcd. for C$_{28}$H$_{28}$FNO$_3$S.1.0 HCl: C, 65.42; H, 5.69; N, 2.73. Found: C, 65.53; H, 5.76; N, 2.77.

Example 4

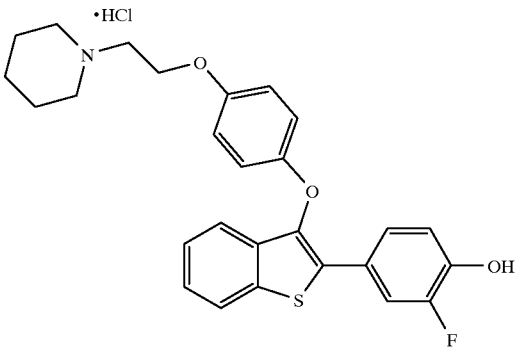

In a manner similar to that used in Example 2, the title compound was prepared in 82% yield and isolated as a white solid. mp 244–246° C. $^1$H NMR (DMSO-d$_6$) d 10.41 (s, 1H), 7.96 (d, J=7.3 Hz, 1H), 7.47 (m, 1H), 7.37–7.30 (m, 4H), 7.04 (t, J=8.7 Hz, 1H), 6.94–6.87 (m, 4H), 4.31–4.00 (m, 2H), 3.45–3.34 (m, 4H), 2.96–2.90 (m, 2H), 1.75–1.62 (m, 5H), 1.16 (m, 1H). FD mass spec: 463. Anal. Calcd. for C$_{27}$H$_{26}$FNO$_3$S.1.0 HCl: C, 64.85; H, 5.44; N, 2.80. Found: C, 64.83; H, 5.62; N, 2.74.

The following discussions illustrate methods of use for the compounds of formula I in experimental models or in clinical studies. These examples are for the purposes of illustration and are not meant to be limiting in any way.

A. Osteoporosis:

Experimental models of postmenopausal osteoporosis are known in the art. Germane to this invention is the ovariectomized rat model which is provided in U.S. Pat. No. 5,393,763. The compounds of formula I would be active in this model and would demonstrate an effective treatment or prevention of bone loss due to the deprivation of estrogen.

An additional demonstration of the method of treating or preventing osteoporosis due to estrogen deprivation would be as follows: One hundred patients would be chosen, who are healthy postmenopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids six months prior to the study or who have ever taken bis-phosphonates.

Fifty women (test group) would receive 15–80 mg of a compound of formula I, for example, Formulation 1 (above), per day. The other fifty women (control group) would receive a matched placebo per day. Both groups would receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline crosslinks. Blood samples are measured for serum levels of osteocalcin and bone-specific alkaline phosphatase. Baseline measurements would also include a uterine examination and bone mineral density determination by photon absorptiometry.

The study would continue for six months, and each the patients would be examined for changes in the above parameters. During the course of treatment, the patients in the treatment group would show a decreased change in the biochemical markers of bone resorption as compared to the control group. Also, the treatment group would show little or no decrease in bone mineral density compared to the control group. Both groups would have similar uterine histology, indicating the compounds of formula I have little or no utrotrophic effects.

B. Hyperlipidemia:

Experimental models of postmenopausal hyperlipidemia are known in the art. Germane to this invention is the ovariectomized rat model which is detailed in U.S. Pat. No. 5,464,845. Data presented in Table 1 show comparative results among ovariectomized rats, rats treated with 17-α-ethynyl estradiol ($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to estrogen is well recognized in the art.

Not only did the compounds of the present invention reduce serum cholesterol compared to the ovariectomized animals, but the uterine weight was increased to lesser extent than those given $EE_2$. Compared to estrogenic compounds known in the art, the benefit of serum cholesterol reduction while lessening the effect on uterine weight is unusual and desirable.

As expressed in the data below, estrogenicity also was assessed by evaluating the response of eosinophil infiltration into the uterus. The compounds of this invention did not cause as large an increase in the number of eosinophils observed in the stromal layer of the ovariectomized, rat uteri. $EE_2$ caused a substantial and expected increase in eosinophil infiltration.

The data presented in Table 1 reflect the response per treatment group.

TABLE 1

| Compound No. | Dose mg/kg[a] | Uterine Weight % Inc[b] | Uterine Eosinophil (Vmax)[c] | Serum Cholest. % Dec.[d] |
|---|---|---|---|---|
| EE2[e] | 0.1 | 138.8* | 174.3* | 88.1* |
| Example 1 | 0.01 | 9.6 | 2.1 | 12.1 |
|  | 0.1 | 21.9 | 4.8 | 55.6* |
|  | 1.0 | 35.8* | 4.8 | 60.5* |
| Example 2 | 0.1 | 42.7* | 4.5 | 59.6* |
| (free base) | 1.0 | 43.8* | 7.8 | 66.2* |
|  | 10.0 |  | 37.2* | 4.5 59.0* |
| Example 3 | 0.1 | 10.4 | 4.8 | 26.3* |
|  | 1.0 |  | 15.3 | 3.0 45.7* |
|  | 10.0 |  | 3.9 | 1.2 22.9 |
| Raloxifene[f] | 0.1 | 23.5 | 5.4 | 49.3* |

[a]mg/kg PO
[b]Uterine Weight % increase versus the ovariectomized controls
[c]Eosinophil peroxidase, $V_{maxium}$
[d]Serum cholesterol decrease versus ovariectomized controls
[e]17-α-Ethynyl-estradiol
[f]Raloxifene [2-(4-hydroxyphenyl)-6-hydroxybenzo[b]thien-3-yl][4-[2-(1-piperdinyl)ethoxy]phenyl]methanone hydrochloride (see: Jones, ibid.)
*p < .05

An additional demonstration of the method of treating hyperlipidemia due to estrogen deprivation would be as follows: One hundred patients would be chosen, who are healthy postmenopausal women, aged 45–60, and who would normally be considered candidates for estrogen replacement therapy. This would include women with an intact uterus, who have not had a menstrual period for more than six months, but less than six years. Patients excluded for the study would be those who have taken estrogens, progestins, or corticosteroids.

Fifty women (test group) would receive 15–80 mg of a compound of formula I, for example, using Formulation 1, per day. The other fifty women (control group) would receive a matched placebo per day. The study would be a double-blind design. Neither the investigators nor the patients would know to which group each patient is assigned.

A baseline examination of each patient would include serum determination of cholesterol and tri-glyceride levels. At the end of the study period (six months), each patient would have their serum lipid profile taken. Analysis of the data would confirm a lowering of the serum lipids, for example, cholesterol and/or tri-glycerides, in the test group versus the control.

We claim:

1. A compound of formula I

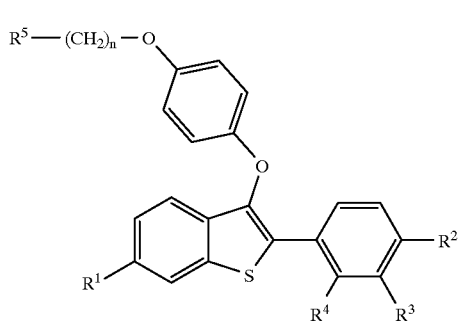

wherein
  $R^1$ is —H, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^2$ is —H, —F, —Cl, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^3$ and $R^4$ are, independently, —H, —F, —Cl, —OH, —O($C_1$–$C_4$ alkyl), —OCOAr where Ar is phenyl or substituted phenyl, —OCO($C_1$–$C_6$ alkyl), —O(CO)O ($C_1$–$C_6$ alkyl), or —OSO$_2$($C_4$–$C_6$ alkyl), with the proviso that only one of $R^2$, $R^3$, and $R^4$ can be hydrogen;

n is 2 or 3; and $R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino;

or a pharmaceutically acceptable salt or solvate thereof.

2. A compound according to claim 1 wherein $R^3$ is methoxy.

3. A compound according to claim 1 wherein $R^3$ is hydroxy.

4. A compound according to claim 1 wherein n is two and $R^5$ is 1-piperidinyl.

5. A compound according to claim 1 wherein said salt thereof is the hydrochloride salt.

6. A compound according to claim 1 selected from the group consisting of 2-(3,4-dimethoxyphenyl)-3-[4-[2-(1-piperidinyl)ethoxy] phenoxy]-6-methoxybenzo[b]thiophene;

2-(3,4-dimethoxyphenyl)-3-[4-[2-(1-piperidinyl)ethoxy] phenoxy]-6-hydroxybenzo[b]thiophene;

2-(3,4-dihydroxyphenyl)-3-[4-[2-(1-piperidinyl)ethoxy] phenoxy]-6-hydroxybenzo[b]thiophene;

2-(3-methoxy-4-fluorophenyl)-3-[4-[2-(1-piperidinyl) ethoxy]phenoxy]-6-hydroxybenzo[b]thiophene;

2-(3-hydroxy-4-fluorophenyl)-3-[4-[2-(1-piperidinyl) ethoxy]phenoxy]-6-hydroxybenzo[b]thiophene;

2-(3-chloro-4-hydroxyphenyl)-3-[4-[2-(1-piperidinyl) ethoxy]phenoxy]-6-hydroxybenzo[b]thiophene;

2-(2-hydroxy-3-hydroxyphenyl)-3-[4-[2-(1-piperidinyl) ethoxy]phenoxy]-6-hydroxybenzo[b]thiophene; and 2-(2-fluoro-3-acetyloxy-4-fluorophenyl)-3-[4-[2-(1-piperidinyl)ethoxy]phenoxy]benzo[b]thiophene citrate;

2-(2-acetyloxy-3-acetyloxyphenyl)-3-[4-[2-(1-piperidinyl)ethoxy]phenoxy]-6-acetyloxybenzo[b] thiophene;

2-(3,4-dihydroxyphenyl)-3-[4-[3-(1-hexamethyleneimino)propopoxy]phenoxy]-6-hydroxybenzo[b]thiophene.

7. A pharmaceutical formulation comprising a compound according to claim 1 in combination with a pharmaceutically acceptable carrier, diluent, or excipient.

8. A method of inhibiting bone loss or bone resorption comprising administering to a patient in need thereof an effective amount of a compound of claim 1.

9. A method according to claim 8 wherein said bone loss or bone resorption is due to menopause or ovariectomy.

10. A method of lowering serum cholesterol levels comprising administering to a patient in need thereof an effective amount of a compound of claim 1.

* * * * *

UNITED STATES PATENT AND TRADEMARK OFFICE
CERTIFICATE OF CORRECTION

PATENT NO. : 5,977,098
DATED : November 2, 1999
INVENTOR(S) : Alan David Palkowitz It is certified that error appears in the above-identified patent and that said Letters Patent is hereby corrected as shown below:

In column 36, between line 3 and 4 insert "2-(3,4-dihydroxyphenyl)-3-[4-[2-(1-piperidinyl)ethoxy]phenoxy]-6-methoxybenzo[b]thiophene;".

Signed and Sealed this

Twelfth Day of September, 2000

Attest:

Q. TODD DICKINSON

Attesting Officer

Director of Patents and Trademarks